United States Patent [19]

Bower

[11] 4,113,753

[45] Sep. 12, 1978

[54] TETRA (BICYCLOHEPTYL) TRANSITION METAL COMPOUNDS

[75] Inventor: Barton Keeley Bower, Nottingham, Pa.

[73] Assignee: Hercules Incorporated, Wilmington, Del.

[21] Appl. No.: 782,265

[22] Filed: Mar. 25, 1977

[51] Int. Cl.$^2$ ................................................ C07F 7/28
[52] U.S. Cl. .......................... 260/429.5; 260/429 CY; 260/438.5 R; 260/439 CY
[58] Field of Search ................. 260/429 CY, 439 CY, 260/429.5, 438.5 R

[56] References Cited

U.S. PATENT DOCUMENTS

| | | | |
|---|---|---|---|
| 3,093,671 | 6/1963 | Ihrman et al. | 260/438.5 R |
| 3,105,084 | 9/1963 | Wilkinson | 260/429 CY |
| 3,704,259 | 11/1972 | Bower | 260/438.5 R |
| 3,705,916 | 12/1972 | Bower | 260/429.3 |

OTHER PUBLICATIONS

Hackh's Chemical Dictionary, 3rd Ed., McGraw-Hill Book Co., N.Y., p. 161, (1944).
Heilbron, Dictionary of Organic Compounds, Oxford University Press., N.Y., VI, pp. 411, 412, (1953).

*Primary Examiner*—Helen M. S. Sneed
*Attorney, Agent, or Firm*—John W. Whitson

[57] ABSTRACT

The compounds of this invention are tetravalent organometallic compounds of transition metals wherein the metal is attached to the bridgehead carbons of four bicyclic radicals, namely, 1-bicyclo[2.2.1]-heptyl radicals which contain an alkylidene group attached to either the $C_2$ or $C_7$ carbon atom. Typical of these compounds is tetrakis-(1-camphenyl) chromium. These organometallic compounds are particularly effective catalysts for the curing of photochemical compositions.

7 Claims, No Drawings

TETRA (BICYCLOHEPTYL) TRANSITION METAL COMPOUNDS

This invention relates to a new class of organometallic compounds. More particularly, it relates to tetravalent compounds of transition metals wherein the metal is attached to the bridgehead carbon of certain bicyclic hydrocarbon radicals containing exocyclic olefinic unsaturation.

Transition metal alkyls wherein the transition metal is from Groups IV-B, V-B, VI-B, VII-B and VIII of the periodic table are known. Where the alkyl ligand is branched alkyl, such as neopentyl, or monocyclic, such as cyclohexyl, the compounds are subject to oxidative or hydrolytic degradation. Where the alkyl ligand contains olefinic unsaturation β,γ to the transition metal, as in allyl, the compounds are even more susceptible to oxidative degradation. Thus, when such compounds are incorporated as catalysts into photochemical formulations, extensive precautions to protect the formulations from oxygen and moisture are necessary. However, where the alkyl ligand is bicyclic, such as norbornyl or camphyl, the compounds are very stable to air oxidation at room temperature and are therefore easily handled and utilized.

Now in accordance with this invention, a unique class of organometallic tetravalent transition metal compounds has been discovered wherein the metal is bound to the bridgehead carbons of four bicyclic hydrocarbon radicals containing an alkylidene group. These new organometallic compounds have the formula $Y_4M$ wherein Y is either a 2-alkylidene-1-bicyclo-[2.2.1]-heptyl radical or a 7-alkylidene-1-bicyclo-[2.2.1]-heptyl radical, either of which can be substituted with up to five methyl groups. Thus, the compounds of this invention have either the formula

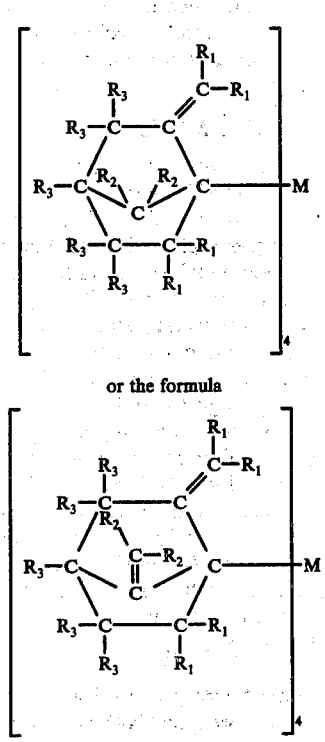

I or the formula

II wherein M is a transition metal selected from Ti, Zr, Hf, V, Cr, Mn, Fe and Co and wherein the R substituents may be hydrogen or from one to five methyl groups, provided that, in formula I, there can be one methyl group attached to $C_6$ or the terminal carbon of the alkylidene group, unless $C_7$ is substituted with one or two methyl groups, in which case there can be no methyl group attached to $C_6$ or the terminal carbon of said alkylidene group, and that, in formula II, there can be one methyl group attached to $C_2$ or $C_6$, unless the terminal carbon of the alkylidene group is substituted with one or two methyl groups, in which case there can be no methyl group attached to $C_2$ or $C_6$.

In other words, in these formulas, one of the $R_1$'s may be methyl when both of the $R_2$'s are hydrogen, but all of the $R_1$'s are hydrogen when one or both of the $R_2$'s are methyl. Even more briefly, only one of the $R_1$'s may be methyl, and then only if both of the $R_2$'s are hydrogen. Exemplary of the alkylidene-1-bicyclo-[2.2.1]-heptyl radicals of the compounds of this invention are:

2-methylidene-1-bicyclo-[2.2.1]-heptyl
2-ethylidene-1-bicyclo-[2.2.1]-heptyl
7-methylidene-1-bicyclo-[2.2.1]-heptyl
7-ethylidene-1-bicyclo-[2.2.1]-heptyl
7-isopropylidene-1-bicyclo-[2.2.1]-heptyl
2-methylidene-3-methyl-1-bicyclo-[2.2.1]-heptyl (also known as 1-isosantenyl)
2-methylidene-4-methyl-1-bicyclo-[2.2.1]-heptyl
2-methylidene-5-methyl-1-bicyclo-[2.2.1]-heptyl
2-methylidene-6-methyl-1-bicyclo-[2.2.1]-heptyl
2-methylidene-7-methyl-1-bicyclo-[2.2.1]-heptyl
7-methylidene-2-methyl-1-bicyclo-[2.2.1]-heptyl
7-ethylidene-3-methyl-1-bicyclo-[2.2.1]-heptyl
7-isopropylidene-3-methyl-1-bicyclo-[2.2.1]-heptyl
2-methylidene-3,3-dimethyl-1-bicyclo-[2.2.1]-heptyl (also known as 1-camphenyl)
2-methylidene-5,5-dimethyl-1-bicyclo-[2.2.1]-heptyl (also known as 1-isofenchenyl)
2-methylidene-7,7-dimethyl-1-bicyclo-[2.2.1]-heptyl (also known as 1-fenchenyl)
2-methylidene-3,4-dimethyl-1-bicyclo-[2.2.1]-heptyl
2-methylidene-4,7,7-trimethyl-1-bicyclo-[2.2.1]-heptyl
2-methylidene-3,3,5-trimethyl-1-bicyclo-[2.2.1]-heptyl
2-methylidene-3,4,5,6-tetramethyl-1-bicyclo-[2.2.1]-heptyl
2-methylidene-3,3,4,5,6-pentamethyl-1-bicyclo-[2.2.1]-heptyl.

These new tetravalent transition metal compounds are surprisingly stable in comparison to previously known compounds containing olefinic unsaturation β,γ to the transition metal and also are surprisingly more active as photocatalysts than the corresponding saturated compounds. As a result, the compounds are very useful as catalysts for the curing of photochemical compositions. Such compositions containing the compounds of this invention are readily prepared in an air atmosphere and exhibit good shelf stability. The compounds of this invention also have the added advantage of being producible in a fewer number of reaction steps than those necessary in preparing the corresponding saturated compounds.

The bridgehead transition metal compounds of this invention can be prepared by the reaction of the corresponding bridgehead lithium compound with a transition metal salt or alkoxide. The bridgehead lithium compound is itself prepared by reaction of the correponding bridgehead halide with metallic lithium. Exemplary bridgehead lithium compounds that can be so prepared and used to prepare the organometallic compounds of this invention are 1-camphenyllithium, 1-fenchenyllithium, 7-methylidene-1-bicyclo-[2.2.1]-heptyllithium, 2-methylidene-4-methyl-1-bicyclo-[2.2.1]-heptyllithium, 2-methylidene-3,3,5-trimethyl-1-bicyclo-[2.2.1]-heptyllithium and 2-methylidene-3,3,4,5,6-pentamethyl-1-bicyclo-[2.2.1]-heptyllithium. Any halide or tertiary butoxide of titanium, zirconium, hafnium, vanadium, chromium, manganese, iron or cobalt can be reacted with the bridgehead lithium compound. Regardless of the valence of the metal in the salt or alkoxide being reacted, the product is always tetravalent. For example, titanium trichloride and titanium tetrachloride both yield tetrakis-(1-camphenyl) titanium, and chromium dichloride and chromium trichloride both yield tetrakis-(1-camphenyl) chromium. In many cases it is advantageous to use an ether complex of the metal salt. Exemplary of the transition metal salts and alkoxides that can be reacted to produce the compounds of this invention are titanium trichloride tetrahydrofuranate (TiCl$_3$.3THF), titanium tetrachloride, titanium tetrafluoride, titanium tetrachloride tetrahydrofuranate (TiCl$_4$.2THF), zirconium tetrachloride etherate (ZrCl$_4$.2Et$_2$O), zirconium tetrabromide, hafnium tetrachloride etherate (HfCl$_4$.2Et$_2$O), vanadium tetrachloride, vanadium tetra(tert-butoxide), vanadium trichloride tetrahydrofuranate (VCl$_3$.3THF), chromium trichloride, chromium trichloride tetrahydrofuranate (CrCl$_3$.3THF), chromium dichloride, chromium difluoride, chromium diiodide, chromium dimethoxide, chromium trimethoxide, chromium tetra(tert-butoxide), manganese dibromide, manganese dichloride, manganese difluoride, manganese trifluoride, manganese dichloride tetrahydrofuranate (MnCl$_2$.1.5THF), ferric chloride, ferrous chloride, ferric chloride etherate (FeCl$_3$.Et$_2$O), cobalt dichloride and cobalt dichloride tetrahydrofuranate (CoCl$_2$.1.5THF).

The reaction between the bridgehead lithium compound and the transition metal salt or alkoxide is carried out in a saturated hydrocarbon diluent such as pentane, hexane, heptane and cyclohexane. The temperature at which the reaction is carried out can be varied widely but generally will be within the range of from about −78° C. to about 100° C. In some cases it is desirable to start the reaction at a low temperature such as −78° C. and then continue it at a higher temperature.

The following examples illustrate the preparation of the organometallic compounds of this invention and their use as photocatalysts.

EXAMPLE 1

Under an atmosphere of nitrogen throughout the reaction, a reaction vessel was charged with 590 mg. of 1-camphenyllithium, 591 mg. of chromium trichloride tris-tetrahydrofuranate, 25 ml. of pentane and 25 ml. of 0.5 cm. borosilicate glass beads. The reaction mixture was tumbled for 6 days at room temperature, after which the pentane insolubles were removed by centrifugation. The pentane solubles then were filtered through a 5-gram column of basic alumina, after which the pentane was removed by evaporation.

The tetrakis-(1-camphenyl) chromium product in the amount of 310 ml., was recrystallized from ethanol/pentane and analyzed: Found: C, 77.89%; H, 10.02%; Cr, 7.5%; Cl, 0. Theoretical: C, 81.03%. H, 10.18%; Cr, 8.77%; Cl, 0. The tetrakis-(1-camphenyl) chromium compound melted at 180° C. and had a maximum at 510 nm in its visible spectrum. In solution in decahydronaphthalene, the compound exhibited a dark purple color at −78° C., a reddish-brown color at 100° C., and a half-life of 19.8 hours at 101° C. under nitrogen.

EXAMPLE 2

A pentane solution containing 167.7 g. of vanadium tetrachloride per liter was purified by centrifuging and decanting to remove insolubles and then by evaporating a portion of the pentane under reduced pressure to remove hydrogen chloride. Under an atmosphere of nitrogen throughout the reaction, a reaction vessel was charged with 1.88 g. of 1-camphenyl lithium and 25 ml. of pentane, and the resulting mixture was stirred at −78° C. To the stirred mixture there then was added 3.3 ml. of the purified vanadium tetrachloride solution, containing 0.55 g. of vanadium tetrachloride.

The resulting reaction mixture was allowed to warm to room temperature. After maintaining at room temperature overnight, the reaction mixture was centrifuged and decanted to separate the insolubles. The recovered solution was then filtered through a 10-gram column of basic alumina, after which the pentane was removed by evaporation. The tetrakis-(1-camphenyl) vanadium compound so produced had a maximum of 552 nm in its visible spectrum and exhibited a bluish-purple color in solution.

EXAMPLES 3–5

Following generally the procedure of Example 1, tetrakis-(1-camphenyl) manganese, tetrakis-(1-camphenyl) titanium and tetrakis-(1-camphenyl) cobalt were prepared from 1-camphenyllithium and manganese dibromide, titanium tetrachloride bis-tetrahydrofuranate and cobalt dichloride tetrahydrofuranate (CoCl$_2$.1.5THF), respectively. Each of the products was identified by its visible electronic spectrum. Solutions of the products exhibited a green color in the case of the manganese compound, a yellow color for the titanium compound and a brown color in the case of the cobalt compound.

EXAMPLE 6

A 4:1 mixture of a polyol-diisocycnate-hydroxyethyl acrylate polyester resin (Uvimer DV53, Polychrome Corporation) and styrene containing 0.2% by weight of the tetrakis-(1-camphenyl) chromium of Example 1 was spread on a glass plate to make a 4 mil film. An identical film was prepared except to use 0.2% by weight of tetrakis-(1-camphyl) chromium [tetrakis-(2,3,3,-trimethyl-1-bicyclo[2.2.1]-heptyl) chromium] in place of the tetrakis-(1-camphenyl) chromium. Each film was passed three times through the light of a high pressure mercury arc lamp, each pass giving an exposure of 6½ seconds. The film containing the camphenyl chromium compound was essentially completely cured and insoluble in acetone, whereas that containing the camphyl chromium compound was only partially cured and was mostly soluble in acetone. A control film containing no catalyst, when exposed in the same manner, was completely soluble in acetone.

EXAMPLE 7

Film compositions were prepared as in Example 6 using 0.2% by weight of tetrakis-(1-camphenyl) vanadium in one composition and 0.2% by weight of tetrakis-(1-norbornyl) vanadium [tetrakis-(1-bicyclo-[2.2.1]-heptyl) vanadium] in the other. Each film was exposed to the irradiation of a medium pressure mercury arc lamp until it was completely cured, as evidenced by insolubility in acetone. The film containing the camphenyl vanadium compound was cured in 18 seconds, whereas that containing the norbornyl vanadium compound required 30 seconds to reach a state of complete cure

What I claim and desire to protect by Letters Patent is:

1. A bicyclic organometallic compound having either the formula

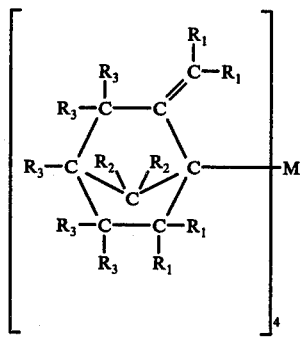

or the formula

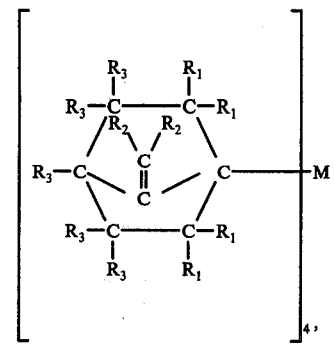

wherein M is a transition metal selected from Ti, Zr, Hf, V, Cr, Mn, Fe and Co and wherein the R substituents are either hydrogen or from one to five methyl groups, with the proviso that only one of the $R_1$'s may be methyl, and then only if both of the $R_2$'s are hydrogen.

2. The compound of claim 1 wherein the bicyclic radical is 1-camphenyl.

3. The compound of claim 2 wherein the transition metal is Cr.

4. The compound of claim 2 wherein the transition metal is V.

5. The compound of claim 2 wherein the transition metal is Mn.

6. The compound of claim 2 wherein the transition metal is Ti.

7. The compound of claim 2 wherein the transition metal is Co.

UNITED STATES PATENT AND TRADEMARK OFFICE
CERTIFICATE OF CORRECTION

PATENT NO. : 4,113,753
DATED      : September 12, 1978
INVENTOR(S): Barton K. Bower (Case 4)

It is certified that error appears in the above-identified patent and that said Letters Patent are hereby corrected as shown below:

Column 1, Formula II,

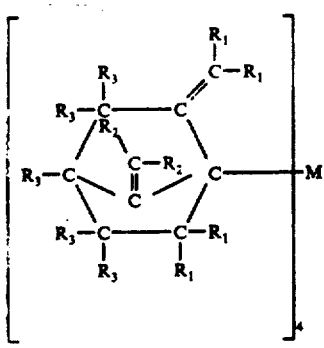 should read 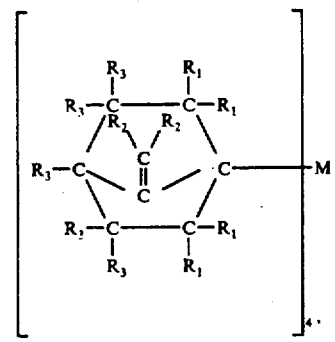

Signed and Sealed this

Twelfth Day of December 1978

[SEAL]

Attest:

RUTH C. MASON
*Attesting Officer*

DONALD W. BANNER
*Commissioner of Patents and Trademarks*